United States Patent [19]

Tersteegen et al.

[11] 4,368,738
[45] Jan. 18, 1983

[54] CANNULA

[76] Inventors: Bernd Tersteegen; Gunter van Endert, both of Karlstrasse 17-19, 4000 Dusseldorf 1, Fed. Rep. of Germany

[21] Appl. No.: 249,357

[22] Filed: Mar. 31, 1981

[30] Foreign Application Priority Data

Apr. 5, 1980 [DE] Fed. Rep. of Germany ....... 3013384

[51] Int. Cl.³ ............................................ A61M 25/00
[52] U.S. Cl. .................................... 604/180; 128/221; 128/329 R; 128/339; 604/272; 604/275
[58] Field of Search ............... 128/348, 347, 221, 314, 128/329, 329 A, 339, 361; 27/24 A

[56] References Cited

U.S. PATENT DOCUMENTS

| 1,749,919 | 3/1930 | Mierley | 128/221 |
| 2,751,907 | 6/1956 | Hickey | 128/221 |
| 3,924,617 | 12/1975 | Ferro | 128/221 |

Primary Examiner—Stephen C. Pellegrino
Attorney, Agent, or Firm—Dressler, Goldsmith, Shore, Sutker & Milnamow, Ltd.

[57] ABSTRACT

An improved dialysis cannula includes an obliquely sharpened point formed by an oblique ground surface. The point includes a front portion which is disposed at an obtuse angle to the remainder of the ground surface, thereby providing a lancet-like front portion which facilitates proper insertion of the cannula into the blood vessel of a patient.

10 Claims, 6 Drawing Figures

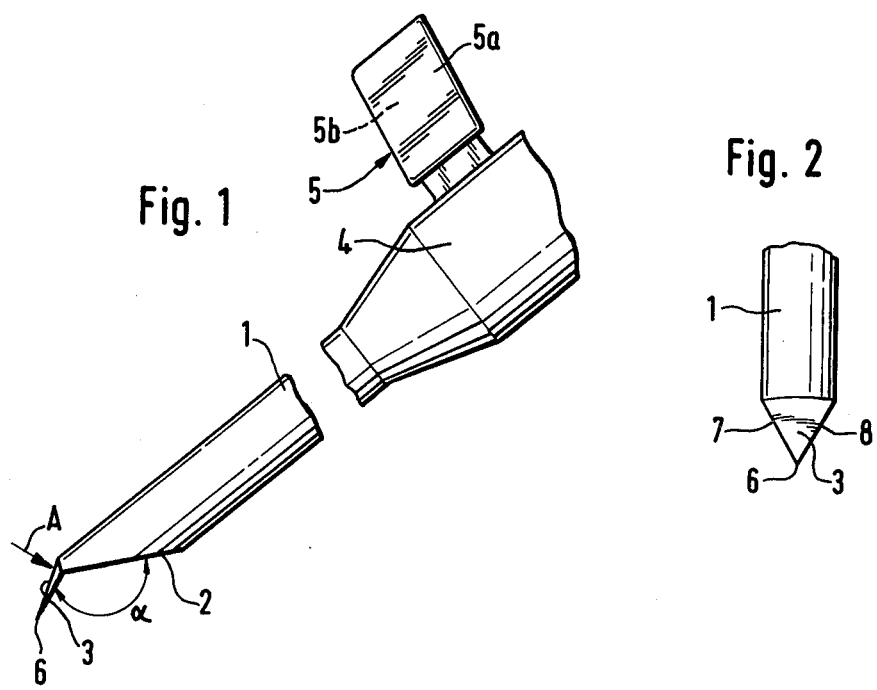
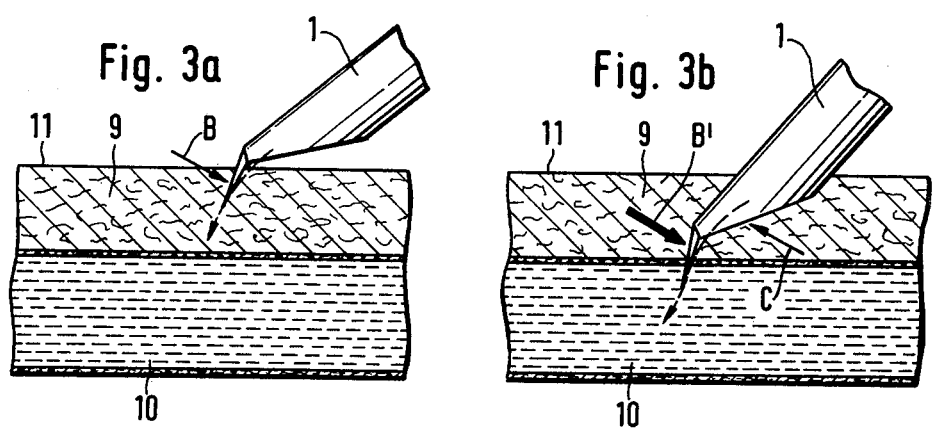
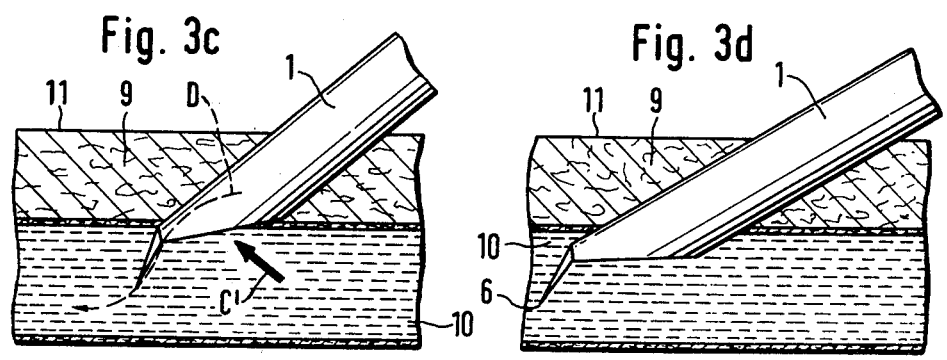

CANNULA

BACKGROUND OF THE INVENTION

The invention relates to a cannula, especially a dialysis cannula, with an obliquely sharpened point.

Cannulas with an obliquely and acutely sharpened point are usually used in medical practice in puncturing body cavities and blood vessels for the purpose of withdrawing or introducing body fluid (e.g. blood) or medicines. The structural design of the cannula, especially of the cannula point, is of particular importance, as is the technique of the manufacturing process in the case of so-called dialysis cannulas. The latter are cannulas which have to be repeatedly introduced into blood vessels of a patient with continual kidney failure for the purpose of connection to the artificial kidney. Each time the patient receives artificial kidney treatment (usually three times a week for life) two cannulas have to be introduced into one of the patient's blood vessels which has been specially surgically prepared before the beginning of the first treatment. The cannulas then remain in the blood vessel for four to eight hours for the duration of a single treatment. The cannulas impede the patient's freedom of movement and involve the danger of a perforating injury to the vessel wall. The latter is particularly important since the patient's blood must be made temporarily incoagulable during extrabodily circulation in order to prevent the formation of clots.

Dialysis cannulas have an essentially larger outer diameter (approximately 1.6 to 2.2 mm) than the usual injection cannulas. Cannulas with ultrathin wall thicknesses (0.05 to 0.1 mm) are also manufactured at present, in order to obtain the smallest possible outer diameter with the same inner diameter.

Cannulas can now be sharpened such that relatively small forces, which act on the cannula point during puncture, are perceptible and contribute to the success of the puncture attempt.

As the treatment procedure with the artificial kidney is, in the long run, the most expensive medical therapy, the manufacturing costs of dialysis cannulas must of course be favorable. A further consideration is that the patient suffering with a chronic kidney disease can only survive as long as dialysis cannulas can be introduced into his blood circulation. The cannulas must therefore be designed such that the blood vessels which are to be punctured are continuously treated with care. This relates both to the moment of puncture and to the entire period of time during which the cannula remains in the very sensitive blood vessel.

For reasons of economy, during largely automated production the cannulas are usually produced such that thin-walled, cylindrical high-quality tubules are initially sharpened or ground more or less obliquely to the longitudinal axis. In a subsequent working step two so-called bevels are made by sharpening the front part of the inclination to form a point of the oblique ground surface which facilitates puncturing.

The cannula is inserted such that the oval opening provided by the oblique ground surface is turned away from the surface of the skin. The following problems arise in the case of this so-called "normal cannula position" when puncturing the blood vessel and during the considerably long period in which the cannula remains in the blood vessel.

When viewed from the side, the cannula has an unequal-sided wedge shape as a result of its oblique ground surface. During puncture, or when tissue and the vessel wall are separated, force components thus act on the cannula point and tend to make the puncture path of the cannula relatively steep with respect to the longitudinal axis of the blood vessel. Whereas the resultant quick penetration into the blood vessel is desirable, further advance entails the danger of penetrating or cutting into the opposite vessel wall. The person performing the puncture must therefore exercise caution and carefully manipulate the cannula to reduce the pressure exerted on it after it has penetrated the wall of the blood vessel to prevent penetration of the opposite vessel wall. Proper performance of this technique depends considerably on the experience of the person performing the insertion.

In the "normal cannula position" the oval opening of the cannula is turned away from the skin during puncturing and therefore perceptible by the patient when the puncture is performed. When the cannula is in this position, the puncture leaves a semi-circular incision in the skin, tissue and vessel wall whose diameter corresponds approximately to the outer diameter of the cannula. In the case of thick-walled cannulas (wall thickness approximately 0.15 to 0.2 mm), the resulting tissue flap slides on the cannula wall, over the end of the ground surface and onto the cannula body. However in the case of modern cannulas with a large inner diameter and a relatively thin wall (0.05 to 0.1 mm), the tissue flap falls into the lumen of the cannula and is either cut off by the rear portion of the oval of the ground surface of the cannula (so-called "coring"), whereby the piece of tissue is punched out and possibly conveyed into the bloodstream, or the tissue flap is not cut off in the case of cannulas which are pretreated by so-called "anti-coring" at the rear of the oval, but is folded back, which is experienced as discomfort by the patient during puncturing.

A further disadvantage lies in the following. Depending upon the varying spacing between the skin surface and the blood vessel, the longitudinal axes of the cannula and of the blood vessel are always disposed, with respect to each other, at an angle which is acute to a greater or lesser degree. As a result of the eccentricity of the ground surface of the cannula, the part which projects furthest into the blood vessel, i.e. the sharp point, is next to the opposite vessel wall, as a result of which there is a danger of injury. This circumstance frequently causes perforations of the vessel wall with the formation of a local haematoma both during puncturing and when the cannula remains in the vessel for a fairly long period.

Blood vessels frequently run relatively close to the surface of the skin. In this case, the front part of the ground surface of the cannula penetrates the blood vessel while the rear oval may still lie above the surface of the skin. There is thus a connection between the blood vessel and the exterior of the skin surface and external environment via the lumen of the cannula. As a result, an amount of blood flows out onto the skin surface, particularly when the blood vessel is artificially filled to congestion, i.e., to increase in the inner pressure. In general this is at least unpleasant, but is dangerous in treatment with an artificial kidney, as many of these patients are carriers of the so-called "serum hepatitis." This illness is essentially passed on by blood or the agent of disease which is in most cases contained therein.

SUMMARY OF THE INVENTION

The object of the invention is essentially to provide a cannula of the type referred to above, in which the described disadvantages do not occur even if the cannula has extremely thin walls. The invention is based on the following considerations.

It is not absolutely necessary that cannulas only be inserted in the described manner called "normal cannula position." Although this cannula position is used world-wide in practically 100% of cases, it is however also possible to turn the cannula through 180° about its longitudinal axis and to perform the puncture in this position (subsequently called "reverse cannula position"). The opening of the cannula faces the surface of the skin in this reverse cannula position. Unlike the normal cannula position, the cannula point in the reverse cannula position no longer tends to rapidly penetrate the blood vessel, but rather to slide over the resilient vessel wall. This "unwillingness" of the cannula point to penetrate the blood vessel leads, particularly when unskilled persons are involved, to an increased risk of not finding the vessel, or of experiencing more difficulty in doing so. However, an advantage of the reverse cannula position lies in the fact that parts of skin and tissue cannot fall into the cannula opening owing to the force of gravity. The cannula is therefore inserted in a smoother manner and the patient is thus guaranteed more safety and less pain and discomfort. In the case of this cannula position the sharp point is also removed earlier from the vessel wall, so that there is not such a great danger of injury. Furthermore, in the case of the reverse cannula position the obliquely sharpened opening of the cannula lies upon the skin. This automatically leads to a considerable sealing effect against the external environment when the cannula point penetrates the blood vessel. As a result, only a little, or usually no blood flows out.

The above-mentioned disadvantage of the "reverse cannula position" is avoided according to the subject invention in that the cannula is angled in the front portion of the oblique ground surface such that there is an obtuse angle between the slant portion of the oblique ground surface and the angled portion. The front portion can be formed with a downward kink or bend. The front portion preferably forms approximately the front one-third of the obliquely sharpened cannula point.

As a result of the design of the ground surface of the cannula according to the subject invention, the cannula is essentially inserted in two stages: The forces which initially act on the angled front portion of the ground surface of the cannula force the sharp cannula point toward and through the vessel wall. Following the entry of the angled front portion into the vessel the forces which act upon the rear portion of the ground surface of the cannula act to drive the cannula point "upwards" again, i.e. away from the opposite vessel wall, such that the acute angle defined between the longitudinal axes of the cannula and blood vessel is lessened. The cannula point thus follows, in an ideal manner, an approximately S-shaped curved path, as long as the other forces, acting in the direction of the longitudinal axis of the cannula, are maintained substantially neutral. The cannula is thereby practically automatically "threaded" or inserted into the blood vessel. Furthermore, the sharp point of the cannula is disposed toward the center of the blood vessel when it is in the end position, whereby contact of the sharp point with the opposite vessel wall is effectively prevented.

The cannula according to the subject invention can be manufactured in a simple manner in that the front one-third of the ground surface of the cannula is pressed or deformed toward the opening so as to produce an obtuse angle between the slant and the angled portions. The front part is preferably angled in a more or less sharp-cornered way in the manner of a kink or bend. The front portion forming the cannula point is shaped like a triangle, the base line of which, remote from the point, is not necessarily curved in accordance with the curve at the circumference of the cannula tube, but is straightened as a result of the kink or bend. Thus, the triangular front portion has a slightly curved or essentially planar surface. This part of the cannula point is thus given the shape of a triangular lancet, whose sides, entending to a point, are acutely sharpened. When using the cannula according to the invention and the reverse cannula position, the skin or tissue incision does not have a semi-circular shape, but extends in a relatively straight line and can therefore be compared to the puncture or incision of a lancet or a scalpel. This leads to an improved acclimation of the wound edges, as a result of which the puncture duct is sealed more rapidly (less secondary bleeding) and the wound heals more quickly.

According to a further characteristic feature of the invention, the cannula can be provided with a unilateral or bilateral wing-like handle, which can be rotated with respect to the cannula about its longitudinal axis. The handle serves to manipulate the cannula during puncturing, and can subsequently be used in order to reliably keep the cannula in place. According to another embodiment of the handle, the latter is unilateral and not rotatable with respect to the cannula. In this embodiment of the invention, the handle is advantageously attached to the side of the cannula which is remote from the face of the oval cannula opening. When the puncture has been performed, the handle and the cannula are rotated about the longitudinal axis of the cannula through 90° in either direction and held in place on the skin. The reverse cannula position during puncturing is determined by the handle which is so-positioned on the cannula. After the handle has been rotated and immobilized, the cannula opening is brought into a position in which there is a minimum risk of the cannula opening adhering to the vessel wall and thus damaging the latter in the case of a deficient blood flow in the blood vessel. The cannula opening is directed "to the side " and not "upwards" or "downwards." In the case of a pressure difference between the inside of a vessel and the external environment caused by the blood pump for the extra-bodily circulation, a blood vessel always closes (collapses) from the "top" to the "bottom" and never "laterally" or from "right" to "left," for anatomical and physical reasons. When using the cannula which is rotated through 90° after the puncture has been performed, the cannula opening is therefore not already "covered" by the vessel wall in the case of slight pressure differences. Instead, the cannula acts to a certain extent as a spacer, and thus keeps the entrance to the cannula opening free for as long as possible and consequently guarantees the greatest possible supply of blood to the blood pump.

According to a further characteristic feature of the subject invention, the handle on the cannula can have on one or both sides a self-sealing adhesive layer provided with a removable cover. This plaster-like adhesive layer enables the cannula to be held in its position after it has been inserted. According to a further characteristic feature of the invention, and the fixed and unilateral handle in particular, the part in which the actual cannula tube is secured can be constructed so as to extend in a slightly conical manner towards the point of the cannula. As a result, after the handle has been placed upon the skin, the direction of the cannula point is predetermined to some extent so as to bring the cannula point or the cannula opening as far as possible into the center of the vessel.

The above-mentioned advantages of the cannula according to the subject invention have been confirmed in laboratory experiments and in experimental clinical tests.

The invention is described in greater detail below with reference to the embodiment represented schematically in the drawing.

BRIEF DESCRIPTION OF THE DRAWINGS

FIG. 1 shows a side view of a cannula according to the subject invention;

FIG. 2 shows a top view onto the angled front region of the cannula taken along the direction of arrow A in FIG. 1;

FIG. 3a to 3d show schematic representations of the puncturing action of the cannula according to FIG. 1.

DESCRIPTION OF THE PREFERRED EMBODIMENT

A dialysis cannula 1 of a relatively thin wall thickness is provided in the front portion with a sharpened slant 2. The cannula point formed by the oblique ground surface is angled approximately in its front third such that there is an obtuse angle $\alpha$ between the slant 2 and the angled front portion 3. The cannula 1 is surrounded at its rear portion by a plastic band 4, to the rear (not illustrated) end of which a tube can be connected in a known manner. A unilateral wing 5 which serves as a handle is provided on the cannula tube holder 4 and is arranged so as to be non-rotatable and such that it projects from the cannula side opposite the slant 2. One or both of the side surfaces of the wing 5a and 5b can also be provided with a self-sealing adhesive layer, which is provided with a removable cover in the manner of a plaster.

As can be seen from FIG. 2, the angled front portion 3 has a slightly curved or essentially planar surface, and can be compared to the structure of a lancet in view of the sharpened sides 7 and 8 which extend towards one another.

With reference to FIGS. 3a 3d, the following illustrates the cannula path during puncture into a blood vessel 10 disposed below a tissue 9. The cannula 1 is held at the cannula tube holder 5 by the person performing the puncture and is then introduced obliquely into the tissue 9 (FIG. 3a). As a result of the angled front portion (3), a force component B is created when the tissue 9 is obliquely punctured and becomes greater (indicated at B' in FIG. 3b) as the cannula penetrates further into the tissue 9. The sharp cannula point is therefore directed "downwardly" in the direction of the wall of the vessel 10. Because of the essentially planar surface of the front portion 3, the incision does not have a semi-circular shape, but extends in an essentially straight line. Following the entry of the front angled one-third of the cannula point into the blood vessel 10 (FIG. 3c), the forces C' acting upon the rear two thirds of the ground surface of the cannula direct the cannula point away from the opposite vessel wall. Once the front third has entered the blood vessel, the force component C' is essentially more effective than the corresponding force component C in the stage represented in FIG. 3b since, following the entry of the angled front portion, the force component B or B' ceases to exist. The cannula point thus follows, in an ideal manner, an approximately S-shaped curved path D (FIG. 3c). As has been confirmed by laboratory experiments and experimental clinical use, the cannula according to the invention is practically automatically threaded or inserted into the blood vessel, without the person performing the puncture having to alter the angle of inclination. As can be seen from FIG. 3d, the sharp point 6 of the cannula is directed toward the center of the blood vessel 10 when it is in its inserted position, thus avoiding any contact of the point 6 with the vessel wall. The cannula tube holder 5, which serves to guide the cannula during insertion, is now swung either to the right or to the left through approximately 90° until the cannula tube holder 5 lies on the skin surface 11 of the patient. The oval cannula opening, which is defined by the slant 2 and angled front portion 3, then faces neither the upper side nor on the underside of the blood vessel, thus considerably decreasing the risk of the cannula opening being covered by the vessel wall in the case of a partial collapse.

What is claimed is:

1. A dialysis cannula having an obliquely sharpened point formed by an oblique ground surface, wherein the point comprises a front portion disposed at an obtuse angle with respect to the ground surface.

2. A cannula as claimed in claim 1, wherein the front portion is distinguished from the rest of the point by a bend.

3. A cannula as claimed in claim 1, wherein the front portion is bent inwardly with respect to the longitudinal axis of the cannula.

4. A cannula as claimed in claim 2, wherein the front portion is approximately one-third of the length of the point.

5. A cannula as claimed in claims 1, 2, or 3, wherein the front portion has a slightly curved surface.

6. A cannula as claimed in claims 1, 2 or 3, wherein the front portion defines an essentially planar surface.

7. A cannula as claimed in any one of claims 1, 2 or 3, and a fixed handle projecting from the side of the cannula opposite the obliquely ground surface.

8. A cannula as claimed in claim 7, wherein the handle has on at least one side a self-sealing adhesive.

9. A dialysis cannula having an obliquely sharpened point formed by an oblique ground surface, wherein the point comprises a front portion disposed at an obtuse angle with respect to the ground surface, wherein the front portion is approximately one-third of the length of the point.

10. A dialysis cannula having an obliquely sharpened point formed by an oblique ground surface, wherein the point comprises a front portion disposed at an obtuse angle with respect to the ground surface, wherein the front portion is bent inwardly with respect to the longitudinal axis of the cannula, wherein the front portion is approximately one-third of the length of the point.

* * * * *